United States Patent
Broome et al.

(10) Patent No.: US 6,726,703 B2
(45) Date of Patent: Apr. 27, 2004

(54) DISTAL PROTECTION DEVICE AND METHOD

(75) Inventors: Thomas E. Broome, Hopkins, MN (US); John M. K. Daniel, Plymouth, MN (US); Thomas R. Hektner, Medina, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 256 days.

(21) Appl. No.: 10/060,125

(22) Filed: Jan. 29, 2002

(65) Prior Publication Data

US 2002/0128681 A1 Sep. 12, 2002

Related U.S. Application Data

(63) Continuation of application No. 09/723,003, filed on Nov. 27, 2000.

(51) Int. Cl.$^7$ .............................................. A61M 29/00
(52) U.S. Cl. ....................................................... 606/200
(58) Field of Search ................................ 606/200, 113, 606/114, 127, 159

(56) References Cited

U.S. PATENT DOCUMENTS

| | | |
|---|---|---|
| 3,592,186 A | 7/1971 | Oster |
| 3,683,904 A | 8/1972 | Forster |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,706,671 A | 11/1987 | Weinrib |
| 4,723,549 A | 2/1988 | Wholey et al. |
| 4,728,319 A | 3/1988 | Masch |
| 4,790,812 A | 12/1988 | Hawkins, Jr. et al. |
| 4,794,928 A | 1/1989 | Kletschka |
| 4,873,978 A | 10/1989 | Ginsburg |
| 4,921,484 A | 5/1990 | Hillstead |
| 4,926,858 A | 5/1990 | Gifford, III et al. |
| 4,969,891 A | 11/1990 | Gewertz |

(List continued on next page.)

FOREIGN PATENT DOCUMENTS

| | | |
|---|---|---|
| DE | 4030998 | 10/1991 |
| EP | 0 737 451 A1 | 10/1996 |
| GB | 2 020 557 B | 1/1983 |
| SU | 764684 | 9/1980 |
| WO | WO 94/24946 | 11/1994 |
| WO | WO 96/01591 | 1/1996 |
| WO | WO 98/02084 | 1/1998 |
| WO | WO 98/02112 | 1/1998 |
| WO | WO 33443 | 8/1998 |
| WO | WO 98/39053 | 9/1998 |
| WO | WO 98/50103 | 11/1998 |
| WO | WO 99/23976 | 5/1999 |

OTHER PUBLICATIONS

Lund et al., "Long–Term Patency of the Ductus Arteriosus After Balloon Dilation: an Experimental Study," *Laboratory Investigation*, vol. 69, No. 4, Apr. 1984, 3 pages.

Cragg et al., "Nonsurgical Placement of Arterial Endoprostheses: A New Technique Using Nitinol Wire," *Radiology*, 147:261–263, Apr. 1983.

Cragg et al., "A Nw Percutaneous Vena Cava Filter," *AJR*, 141; Sep. 1983, 4 pages.

*Primary Examiner*—Kevin T. Truong
(74) *Attorney, Agent, or Firm*—Jones Day

(57) ABSTRACT

A device adapted for deployment in a body vessel for collecting floating debris and emboli in a filter. The device includes a collapsible proximally tapered frame for operably supporting the filter between a collapsed insertion profile and an expanded deployment profile. The tapered collapsible frame includes a mouth which is sized to extend to walls of the body vessel in the expanded deployed profile to seal the filter relative to the body vessel for collecting debris floating in the body vessel.

17 Claims, 12 Drawing Sheets

U.S. PATENT DOCUMENTS

| | | | |
|---|---|---|---|
| 4,998,539 A | 3/1991 | Delsanti | |
| 5,002,560 A | 3/1991 | Machold et al. | |
| 5,011,488 A | 4/1991 | Ginsburg | |
| 5,071,407 A | 12/1991 | Termin et al. | |
| 5,100,423 A | 3/1992 | Fearnot | |
| 5,102,415 A | 4/1992 | Guenther et al. | |
| 5,108,419 A | 4/1992 | Reger et al. | |
| 5,133,733 A | 7/1992 | Rasmussen et al. | |
| 5,190,546 A | 3/1993 | Jervis | |
| 5,190,555 A | 3/1993 | Wetter et al. | |
| 5,329,942 A | 7/1994 | Gunther et al. | |
| 5,354,310 A | 10/1994 | Garnic et al. | |
| 5,370,657 A | 12/1994 | Irie | |
| 5,376,100 A | 12/1994 | Lefebvre | |
| 5,415,630 A | 5/1995 | Gory et al. | |
| 5,421,832 A | 6/1995 | Lefebvre | |
| 5,456,667 A | 10/1995 | Ham et al. | |
| 5,476,104 A | 12/1995 | Sheahon | |
| 5,549,626 A | 8/1996 | Miler et al. | |
| 5,658,296 A | 8/1997 | Bates et al. | |
| 5,662,671 A | 9/1997 | Barbut et al. | |
| 5,695,519 A | 12/1997 | Summers et al. | |
| 5,709,704 A | 1/1998 | Nott et al. | |
| 5,746,758 A | 5/1998 | Nordgren et al. | |
| 5,769,816 A | 6/1998 | Barbut et al. | |
| 5,779,716 A | 7/1998 | Cano et al. | |
| 5,792,300 A | 8/1998 | Inderbitzen et al. | |
| 5,814,064 A | 9/1998 | Daniel et al. | |
| 5,817,102 A | 10/1998 | Johnson et al. | |
| 5,827,324 A | 10/1998 | Cassell et al. | |
| 5,833,644 A | 11/1998 | Zadno-Azizi et al. | |
| 5,833,650 A | 11/1998 | Imran | |
| 5,846,260 A | 12/1998 | Maahs | |
| 5,876,367 A | 3/1999 | Kaganov et al. | |
| 5,893,867 A | 4/1999 | Bagaoisan et al. | |
| 5,895,399 A | 4/1999 | Barbut et al. | |
| 5,911,734 A | 6/1999 | Tsugita et al. | |
| 5,954,745 A | 9/1999 | Gertler et al. | |
| 5,976,172 A | 11/1999 | Homsma et al. | |
| 5,980,555 A | 11/1999 | Barbut et al. | |
| 5,989,281 A | 11/1999 | Barbut et al. | |
| 5,997,557 A | 12/1999 | Barbut et al. | |
| 6,001,118 A | 12/1999 | Daniel et al. | |
| 6,010,522 A | 1/2000 | Barbut et al. | |
| 6,068,645 A | 5/2000 | Tu | |
| 6,086,577 A | 7/2000 | Ken et al. | |
| 6,086,605 A | 7/2000 | Barbut et al. | |
| 6,090,097 A | 7/2000 | Barbut et al. | |
| 6,117,154 A | 9/2000 | Barbut et al. | |
| 6,136,016 A | 10/2000 | Barbut et al. | |
| 6,179,851 B1 | 1/2001 | Barbut et al. | |
| 6,235,045 B1 | 5/2001 | Barbut et al. | |
| 6,277,139 B1 | 8/2001 | Levinson et al. | |
| 6,309,399 B1 | 10/2001 | Barbut et al. | |
| 6,371,971 B1 * | 4/2002 | Tsugita et al. | 606/200 |
| 6,468,291 B2 | 10/2002 | Bates et al. | |
| 6,551,341 B2 * | 4/2003 | Boylan et al. | 606/200 |
| 6,592,606 B2 * | 7/2003 | Huter et al. | 606/200 |

\* cited by examiner

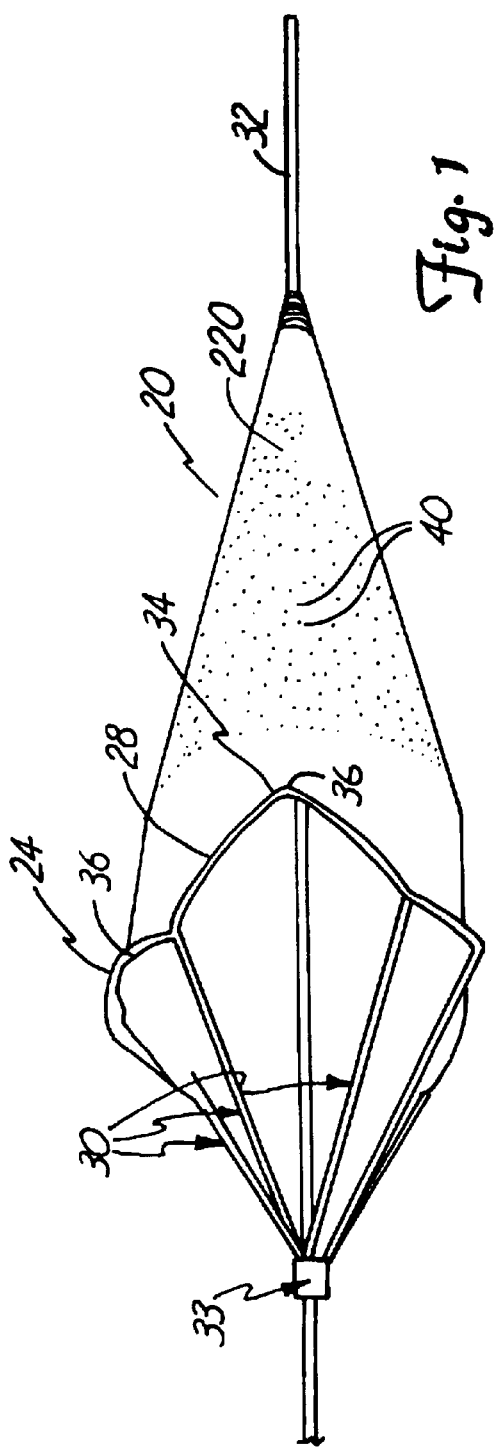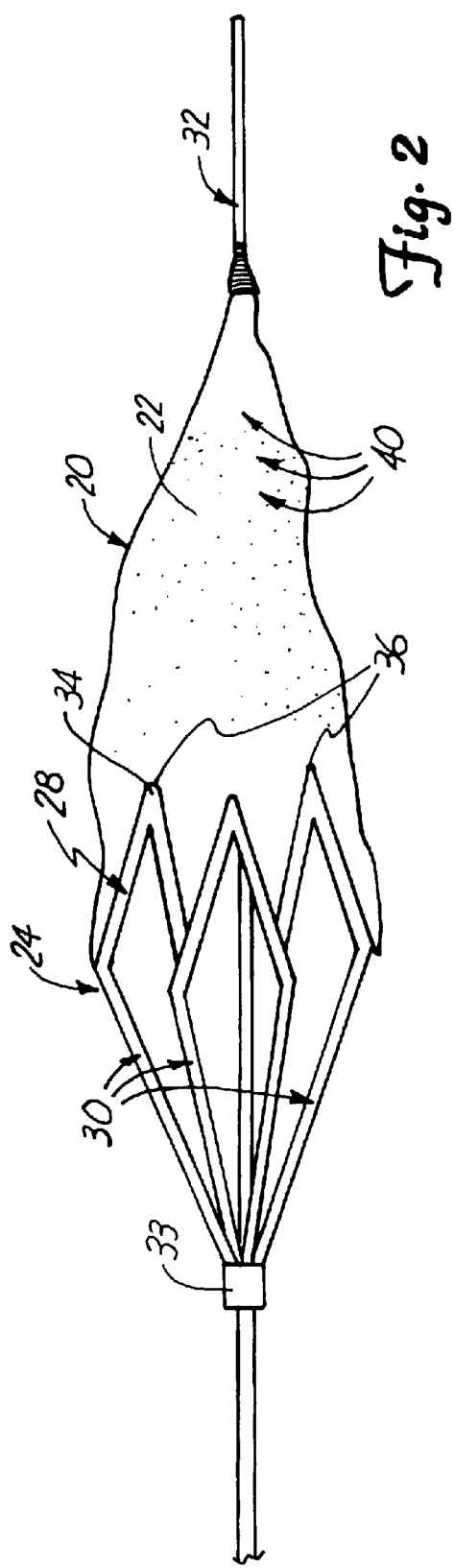

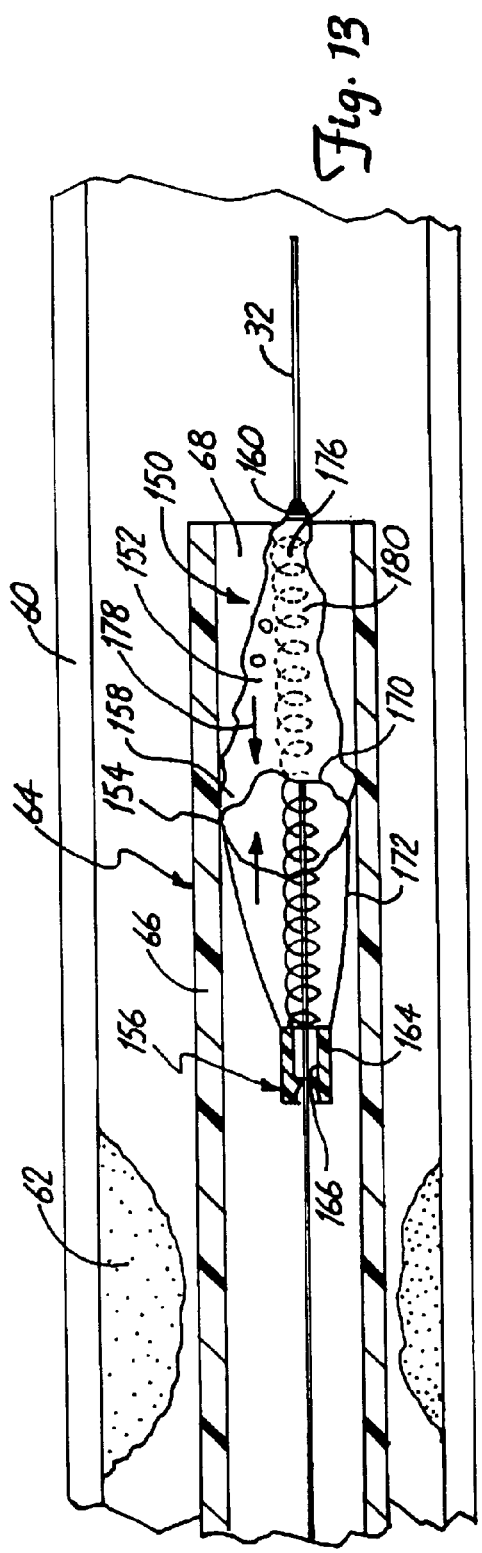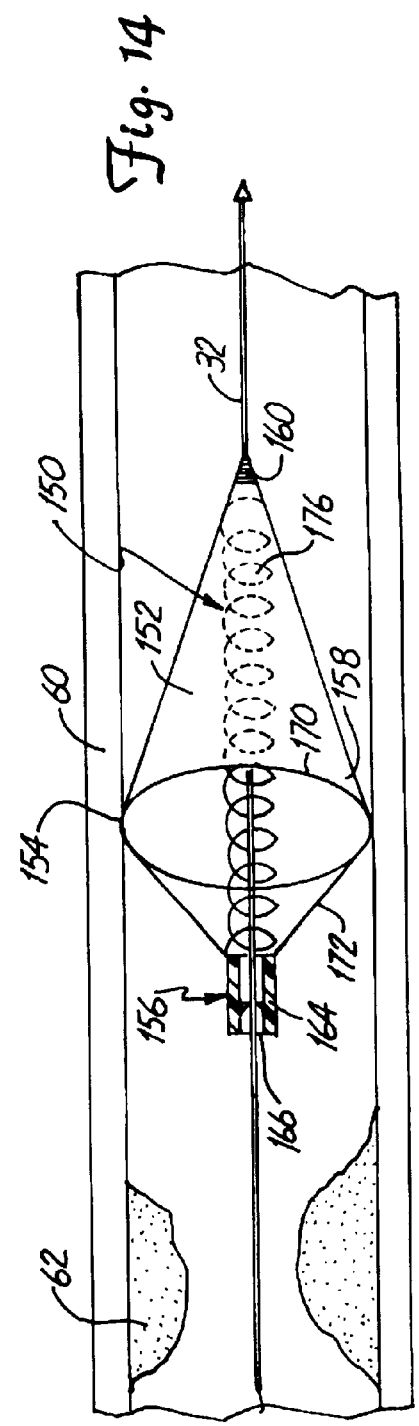

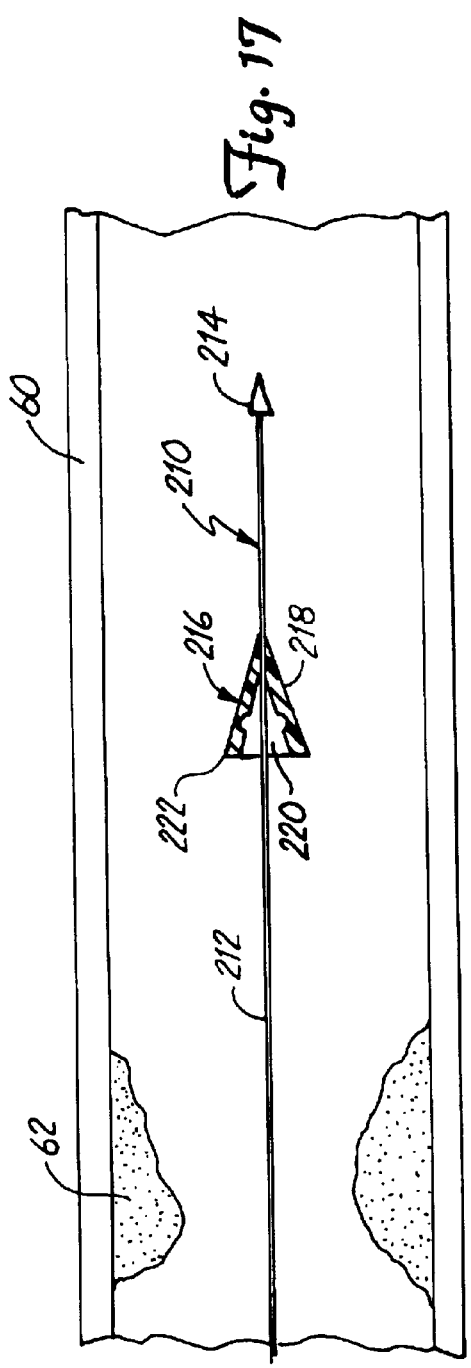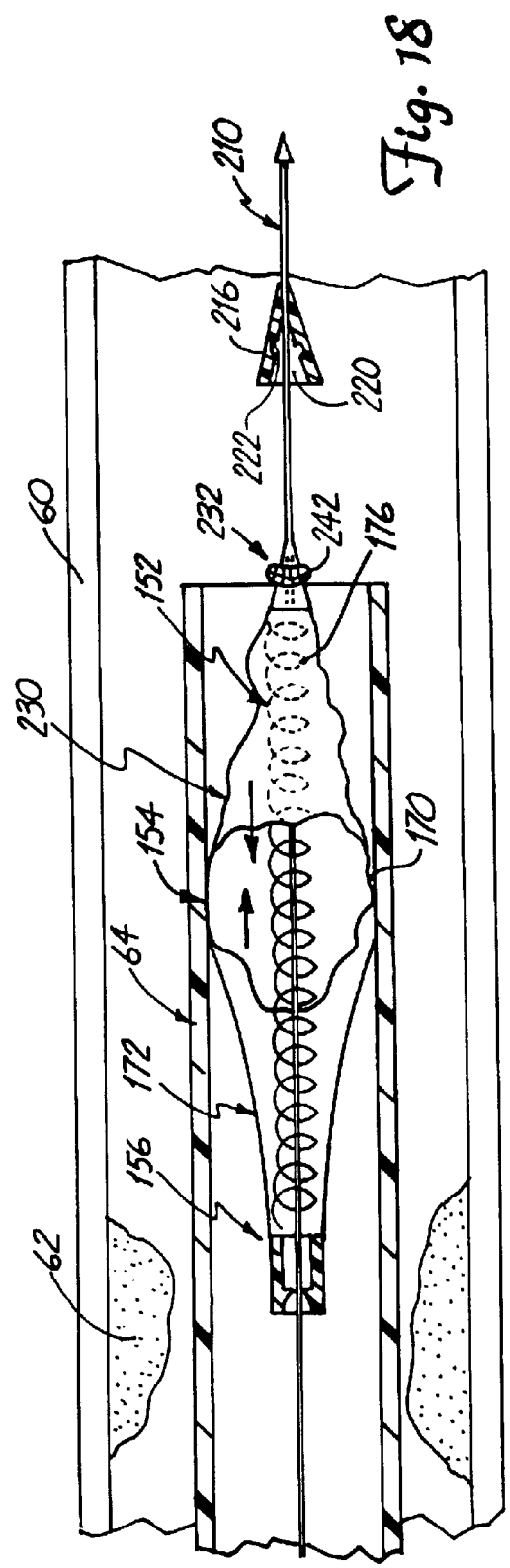

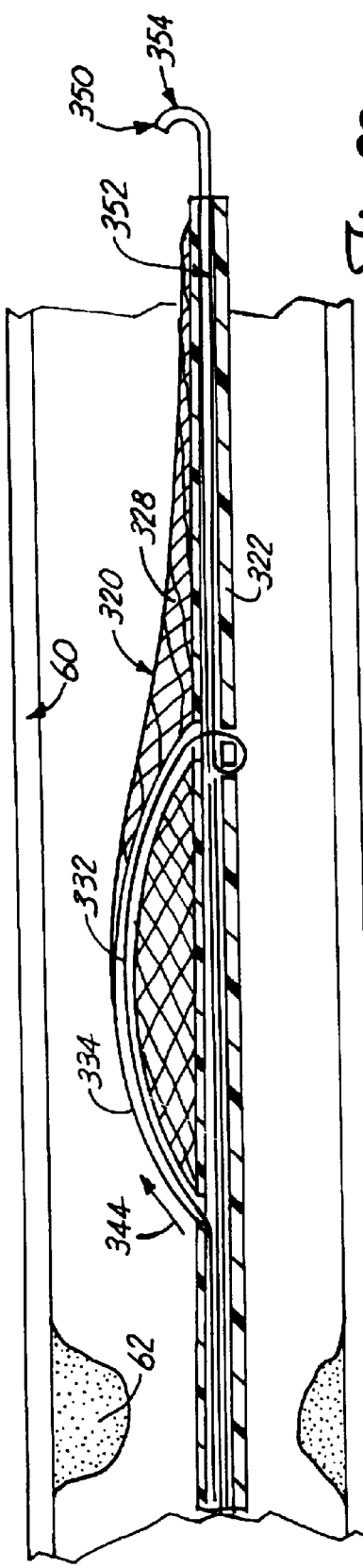
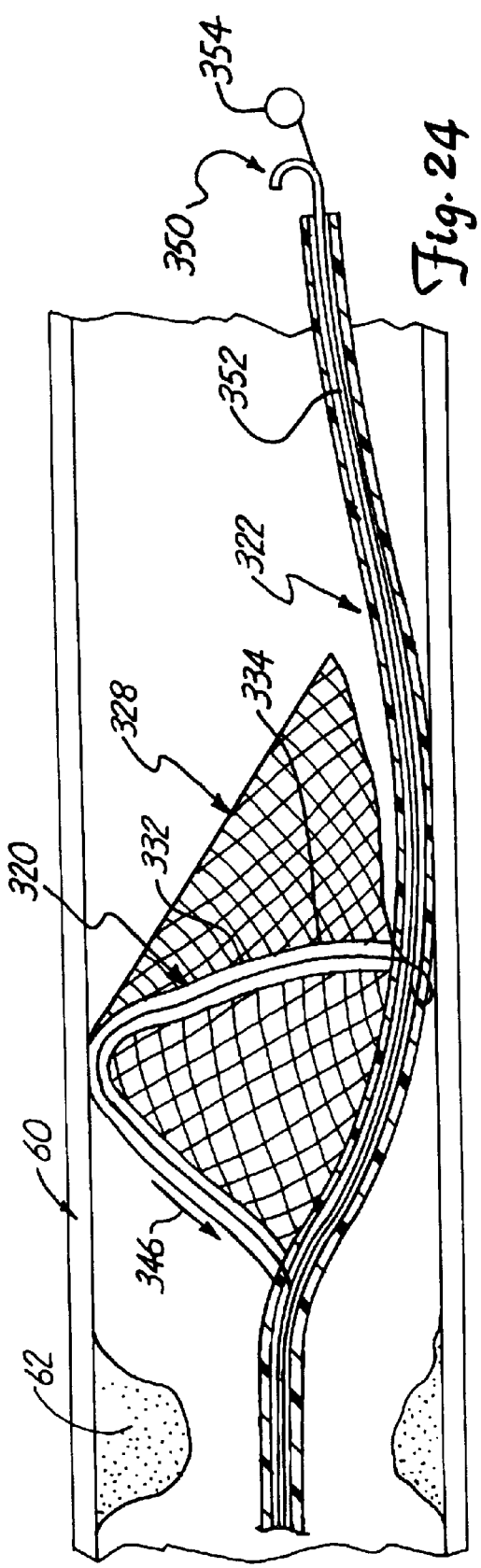

DISTAL PROTECTION DEVICE AND METHOD

CROSS-REFERENCE TO RELATED APPLICATION

This application is a continuation of, and claims priority to, copending application Ser. No. 09/723,003, filed Nov. 27, 2000; now pending which claims priority to application Ser. No. 09/035,740, filed Mar. 5, 1998, now U.S. Pat. No. 6,152,946; application Ser. No. 08/943,358, filed Oct. 3, 1997, now U.S. Pat. No. 6,001,118; and application Ser. No. 08/810,825, filed Mar. 6, 1997, now U.S. Pat. No. 5,814,064.

BACKGROUND OF THE INVENTION

The present invention deals with an emboli capturing system. More specifically, the present invention deals with an emboli capturing system and method for capturing embolic material in a blood vessel during an atherectomy or thrombectomy procedure.

Blood vessels can become occluded (blocked) or stenotic (narrowed) in a number of ways. For instance, a stenosis may be formed by an atheroma, which is typically a harder, calcified substance which forms on the lumen walls of the blood vessel. A stenosis may also be formed of a thrombus material, which is typically much softer than an atheroma but can nonetheless cause restricted blood flow in the lumen of the blood vessel. Thrombus formation can be particularly problematic in a saphenous vein graft ("SVG").

Two different procedures have been developed to treat a stenotic lesion (stenosis) in vasculature. One is deformation of the stenosis to reduce the restriction within the lumen of the blood vessel. This type of deformation, or dilatation, is typically performed using balloon angioplasty.

Another method of treating stenotic vasculature is to attempt to completely remove the entire stenosis, or enough of the stenosis to relieve the restriction in the blood vessel. Removal of the stenotic lesion has been performed through use of radio frequency ("RF") signals transmitted via conductors, and also through use of lasers. Both of these treatments are intended to ablate (i.e., super heat and vaporize) the stenosis. Removal of the stenosis has also been accomplished using thrombectomy or atherectomy. During thrombectomy and atherectomy, the stenosis is mechanically cut or abraded away from the vessel. However, problems may be encountered during thrombectomy and atherectomy because the stenotic debris which is separated from the stenosis is free to flow within the lumen of the vessel. If the debris flows distally, it can occlude distal vasculature and cause significant problems. If it flows proximally, it can enter the circulatory system and form a clot in the neural vasculature or in the lungs, both of which are highly undesirable.

Prior attempts to deal with the debris or fragments produced during thrombectomy and atherectomy have included cutting the debris into pieces small enough (having a size on the order of a blood cell) that they will not occlude vessels within the vasculature. However, this technique has certain problems. For instance, it is difficult to control the size of the fragments which are severed from the stenotic lesion. Larger fragments may be severed accidentally. Also, since thrombus is much softer than an atheroma, it tends to break up easier when mechanically engaged by a cutting instrument. Therefore, at the moment that the thrombus is mechanically engaged, there is a danger that it can be dislodged in large fragments which would occlude the vasculature.

Another attempt to deal with debris severed from a stenosis is to remove the debris as it is severed, using suction. However, it may be necessary to pull quite a high vacuum in order to remove all of the pieces severed from the stenosis. If the vacuum used is not high enough, all of the severed pieces will not be removed. Further, use of a high vacuum may tend to cause the vasculature to collapse.

A final technique for dealing with the fragments severed during atherectomy of the stenosis is placement of a device distal to the stenosis during atherectomy to catch the pieces of the stenosis as they are severed, and removal of those pieces along with the capturing device when the atherectomy procedure is complete. Such capture devices have included expandable filters which are placed distal of the stenosis to capture stenosis fragments. Problems are also associated with this technique. For example, delivery of such devices in a low-profile pre-deployment configuration can be difficult. Further, some devices include complex and cumbersome actuation mechanisms. Also, retrieving such capture devices, after they have captured emboli may be difficult.

SUMMARY OF THE INVENTION

The present invention provides a device adapted for deployment in a body vessel for collecting emboli. The device includes a proximally-tapered collapsible frame for operably supporting the filter between a collapsed insertion profile and an expanded deployment profile. The tapered frame includes a mouth which is sized to extend to walls of a body cavity in the expanded deployed profile for collecting emboli floating in the body cavity.

BRIEF DESCRIPTION OF THE DRAWINGS

FIG. 1 is a perspective view of an embodiment of a protection device in a radially-expanded deployed profile.

FIG. 2 is a view of the protection device of FIG. 1 in a somewhat collapsed profile.

FIG. 13 is a view of an alternate embodiment of a protection device in a collapsed profile being inserted into a vessel via an insertion sheath.

FIG. 14 is a view of the protection device of FIG. 13 in an expanded deployed profile in a vessel.

FIG. 17 is a view of a guidewire adapted to support an alternate embodiment of a protection device.

FIG. 18 is a view of an alternate embodiment of a protection device in a collapsed profile, inserted into a vessel via an insertion sheath.

FIG. 23 is a view of the protection device of FIG. 22 in a collapsed profile in a vessel.

FIG. 24 is a view of the protection device of FIG. 22 in an expanded deployed profile in a vessel.

Figure 3:
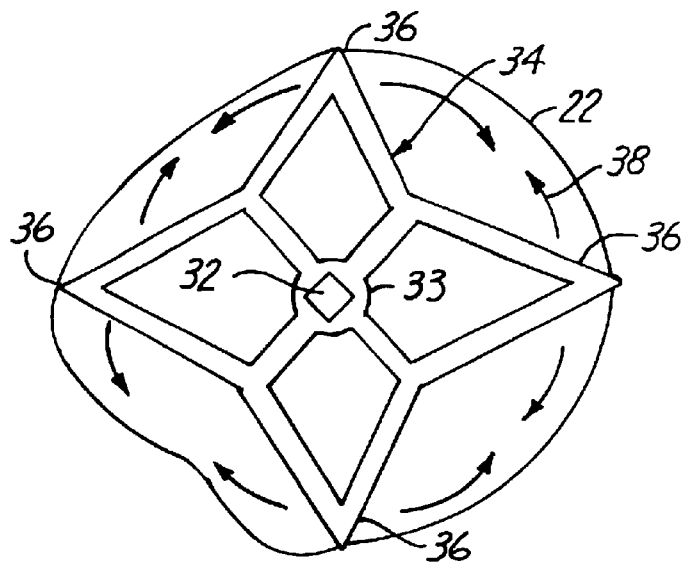
FIG. 3 is an end view of the protection device of FIG. 1 in a radially-expanded deployed profile.

These drawings are for illustrative purposes only and are not necessarily drawn to scale.

DETAILED DESCRIPTION OF THE PREFERRED EMBODIMENTS

The present invention relates to protection devices deployed in a body vessel or cavity for collection of loosened or floating debris such as embolic material dislodged during atherectomy or thrombectomy.

FIGS. 1–7 illustrate an embodiment of a protection device 20 or filter for collecting loosened debris in a body lumen. As illustrated comparatively in FIGS. 1–2, device 20 operates between a closed collapsed profile, adapted for insertion into a body lumen as illustrated in FIG. 2, and an open radially-expanded deployed profile for collecting debris in a body lumen as illustrated in FIG. 1.

Device 20 includes a filter 22 and a collapsible proximally-tapered frame 24. Frame 24 supports filter 22 and is operably coupled to an elongated guidewire 32 or other support device. Frame 24 includes a mouth 28 and a plurality of longitudinally-extending ribs 30. In an expanded profile, mouth 28 is opened and the ribs extend radially outwardly to support mouth 28. Preferably, a collar 33 movably couples the proximal ends of ribs 30 to guidewire 32. Mouth 28 is thus coupled to collar 33 through ribs 30 and is movable between a collapsed profile and an opened deployed profile, as will be explained.

Preferably, filter 22 is generally cone-shaped, having a proximal and a distal end. The distal end is a narrow, "V"-shaped end and is preferably fixedly secured or formed to guidewire 32. The proximal end has a relatively wide opening and is coupled to mouth 28 of frame 24. Preferably, filter 22 is formed of a polymer membrane. In particular, filter 22 is preferably formed of a porous polyurethane material having a plurality of small openings 40. Filter 22 may be constructed of a polyurethane sheet, and openings 40 may be formed in the polyurethane sheet by known laser techniques. Holes or openings 40 are sized to allow blood flow therethrough but restrict flow of debris or emboli floating in the body lumen or cavity. In the embodiment shown, guidewire 32 extends through mouth 28 of device 20 and along the entire length of the device and is fixed to the distal end of filter 22.

Mouth 28 is generally formed of a pleated ring 34 having an expanded dimension to support filter 22 in the opened deployed profile as illustrated in FIGS. 1–3, and a collapsed dimension to support the filter in the closed collapsed profile as illustrated in FIG. 2. FIG. 3 is an end view of device 20 which illustrates pleated ring 34 in an open expanded profile. In the opened expanded profile, ring 34 includes a plurality of folds 36 which are spaced so that the diameter of the pleated ring 34 forms a mouth of sufficient diameter so that an opening to filter 22 conforms to a desired body lumen. Pleated ring 34 is collapsed by closing folds 36 as illustrated by arrows 38 so that adjacent folds 36 are positioned in close proximity. In such a position, the mouth assumes a relatively small dimension to collapse filter 22 for insertion and retrieval. As previously explained, pleated ring 34 is coupled to guidewire 32 via ribs 30 as shown in FIG. 3.

Figure 4:
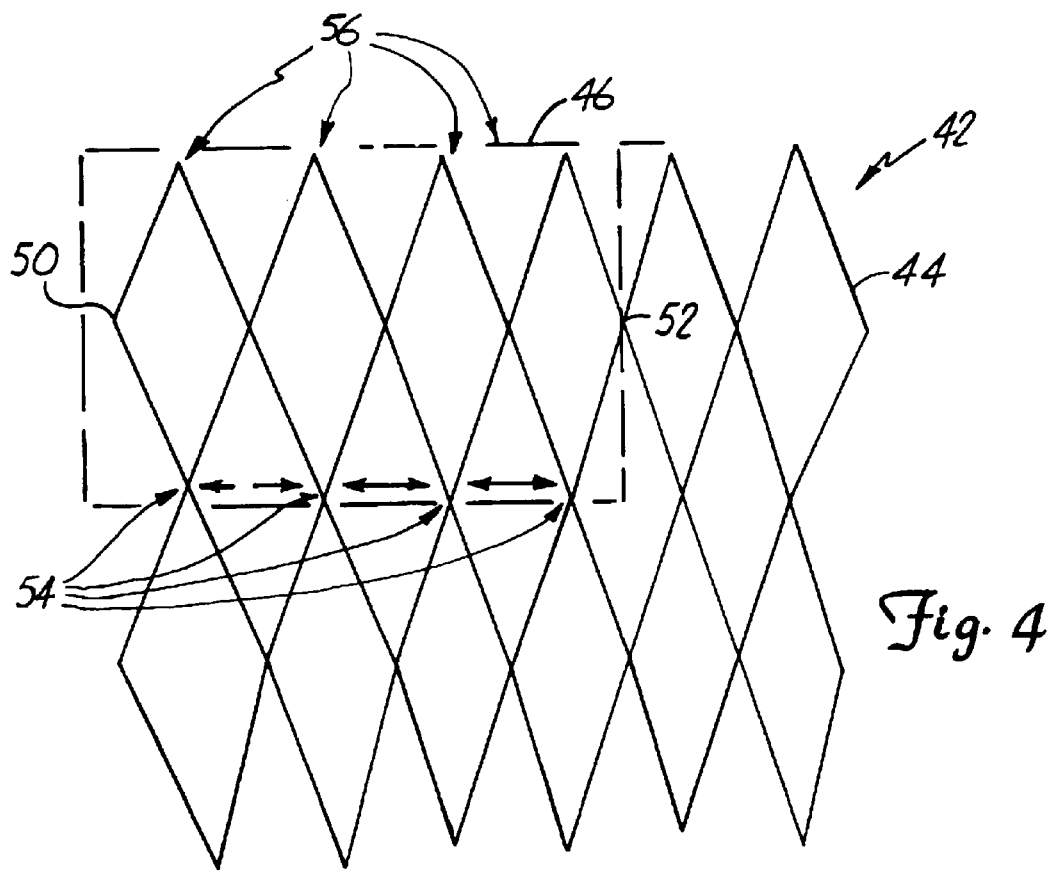
FIG. 4 is a plan view of a wire mesh sheet for construction of a frame of the protection device illustrated in FIG. 1.

FIG. 4 illustrates a process of forming frame 24 and folds 36. Frame 24 may be formed from a wire mesh sheet 42 having a series of rows of generally diamond-shaped structures 44. In one preferred embodiment, a portion 46 of a row is cut from wire mesh sheet 42 to form the frame 24. Portion 46 is rolled and sides 50, 52 are joined to form a continuous circular frame. A series of tips 54 on a first end are joined and coupled to ring 33 which slides over guidewire 26. A series of tips 56 on the second end form pleated ring 34 of mouth 28. In particular, tips 56 form the apex of folds 36, which expand and collapse as illustrated by arrows 38 in FIG. 3, to open and close mouth 28. Preferably, the wire mesh sheet 42 is formed of Nitinol or similar material having sufficient elasticity or resilience, as will be explained. The proximal end of filter 22 is then secured to mouth 28 via an adhesive or other suitable connection method. The distal end of filter 22 is then secured to guidewire 26 via adhesive or other techniques.

Figure 5:
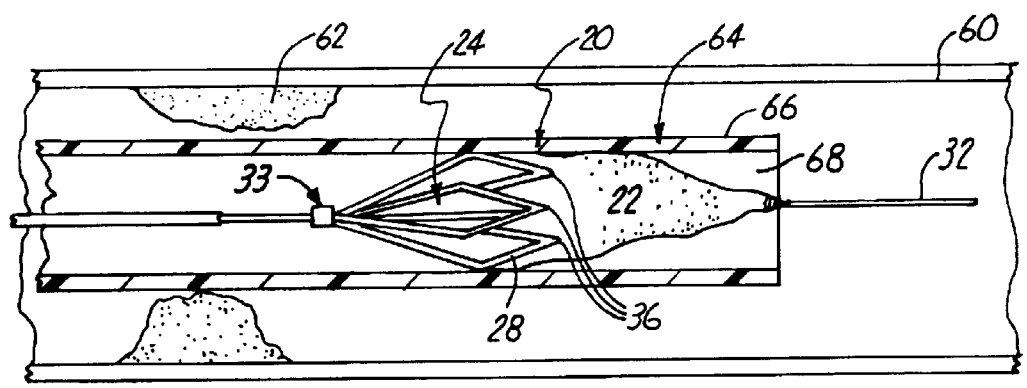
FIG. 5 is a view of the protection device of FIGS. 1–3 in a collapsed profile being inserted through a vessel via an insertion sheath.
Figure 6:
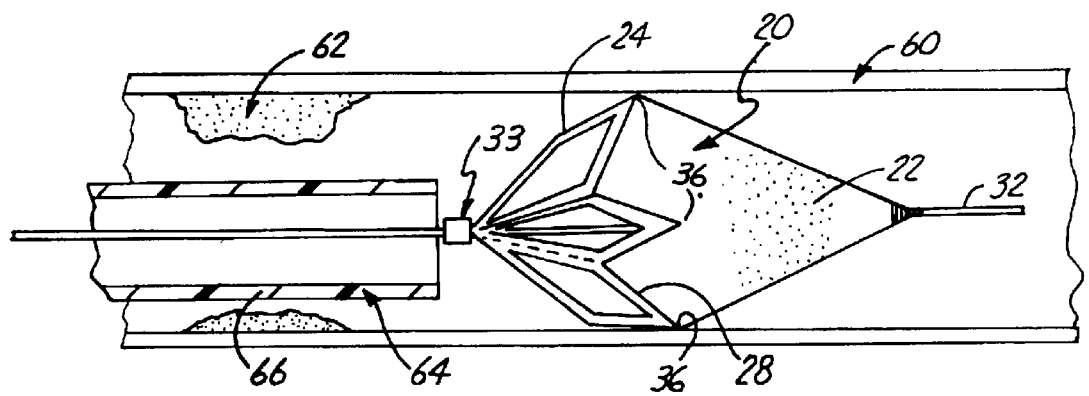
FIG. 6. is a view of the protection device of FIGS. 1–3 inserted into a vessel via the insertion sheath, where the insertion sheath is withdrawn to deploy the protection device for operation.
Figure 7:
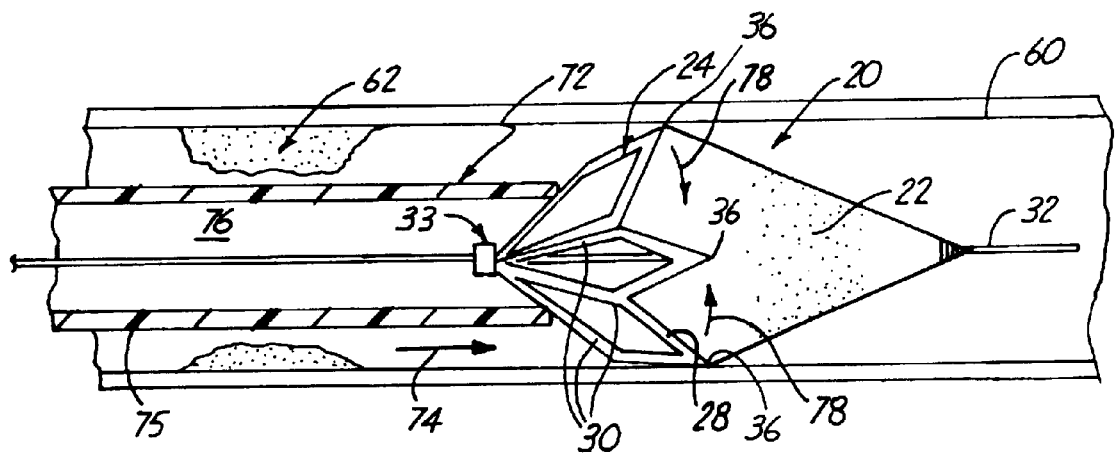
FIG. 7 is a view of the protection device of FIGS. 1–3 operating in a vessel in an expanded deployed profile and illustrating a retrieval sheath for withdrawal of the deployed protection device.

FIGS. 5–7 illustrate operation of protection device 20 which is inserted into a body lumen to collect floating debris or emboli. Briefly, as shown in FIG. 5, device 20 is inserted into a body lumen 60, such as a vascular lumen having a stenosis 62. Device 20 may be deployed distal of the blocked region or stenosis 62 to capture calcified material or substances dislodged during a medical procedure to open the stenosis 62. The stenosis 62 in a coronary vessel may be opened by known medical procedures such as dilatation or atherectomy.

More specifically, as shown in FIG. 5, device 20 is first collapsed and inserted in the collapsed profile into a delivery sheath 64. Sheath 64 is formed of a tubular member 66 including an inner lumen 68 extending therethrough. The profile of sheath 64 is relatively small to facilitate insertion and placement of device 20. Device 20 is placed in lumen 68 for insertion. Folds 36 of frame 24 are collapsed and are maintained in the collapsed profile by the inner surface of lumen 68. In the collapsed profile, collar 33 slides proximally along guidewire 32 to accommodate for the proximal longitudinal movement of ribs 30 as device 20 is collapsed. Once device 20 is inside delivery sheath 64, sheath 64 is inserted through the vasculature of a patient and has its distal end positioned distal of the stenosis or blocked region 62.

To deploy device 20 after it is suitably located, sheath 64 is withdrawn as illustrated by arrow 70 in FIG. 6, thus releasing the pressure exerted via the tube 66 to maintain frame 24 in the collapsed profile. Thus, folds 36 resiliently separate to open mouth 28 and the filter 22 for operation, as illustrated in FIG. 6. Mouth 28 is sized so that when folds 36 separate, mouth 28 conforms to the dimensions of vascular lumen 60. Mouth 28 supports filter 22 relative to the circumference of vascular lumen 60 so that blood flows through the filter and debris and particles floating in the blood are trapped by the filter. In particular, holes 40 of the filter allow blood to flow therethrough, but restrict flow of debris and clotting material so that loosened debris does not migrate and clog alternate body sites.

Preferably, as previously explained, frame 28 is formed of a Nitinol alloy or other elastic material so that the frame "springs" back to an expanded profile after the confining force imparted via sheath 64 is released. The relatively elastic material provides sufficient resilient force for a tight interaction between mouth 28 and lumen 60 to assure that blood flows through filter 22 to capture floating debris and particles.

After deployment, sheath 64 may be completely withdrawn and various treatment devices, such as an angioplasty dilatation catheter, stent delivery catheter or other atherectomy or thrombectomy devices, may be inserted for treatment. The treatment devices are inserted over guidewire 32 for placement relative to the treatment site. After treatment is complete, device 20 is removed as illustrated in FIG. 7.

As shown in FIG. 7, a retrieval sheath 72 is inserted as illustrated via arrow 74 for removal of device 20. Retrieval sheath 72 is formed of a tubular member 75 having a central lumen 76 and a distal opening sized to capture device 20. Retrieval sheath 72 is inserted to align the distal opening of sheath 72 with the proximal end of frame 24. Thereafter, sheath 72 is advanced; or, alternatively, in the embodiment shown, guidewire 32 is retracted, to collapse ribs 30, thereby collapsing mouth 28 and filter 22 as illustrated by arrows 78. In particular, ribs 30 (and the frame 24) are proximally sloped or tapered so that as sheath 72 is advanced over ribs 30, they collapse radially inwardly and collar 33 rides proximally on guidewire 32. As ribs 30 collapse inwardly, frame 24 folds at folds 36 until mouth 28 resides within retrieval sheath 72, or closely proximate the distal end of sheath 72, thereby trapping emboli therein. Device 20 and sheath 72 are then withdrawn from the vasculature.

Although longitudinally sloped ribs 30 are coupled to collar 33 in the device shown, ribs 30 may be directly fixed to guidewire 32 so that the filter is loosely supported in the collapsed profile. Alternatively, the device may be supported via an alternate core wire or guidewire structure (not shown) which is coupled to frame 24 via ribs 30 but unlike guidewire 32 does not extend through the mouth and along the entire length of the filter so that device 20 does not have radial slack in the collapsed profile. Also, although device 20 is shown inserted distal of stenotic region 62 to capture material and debris dislodged during a treatment procedure, device 20 may be deployed in alternate positions for capturing floating debris or particles in other body cavities.

Figure 8:
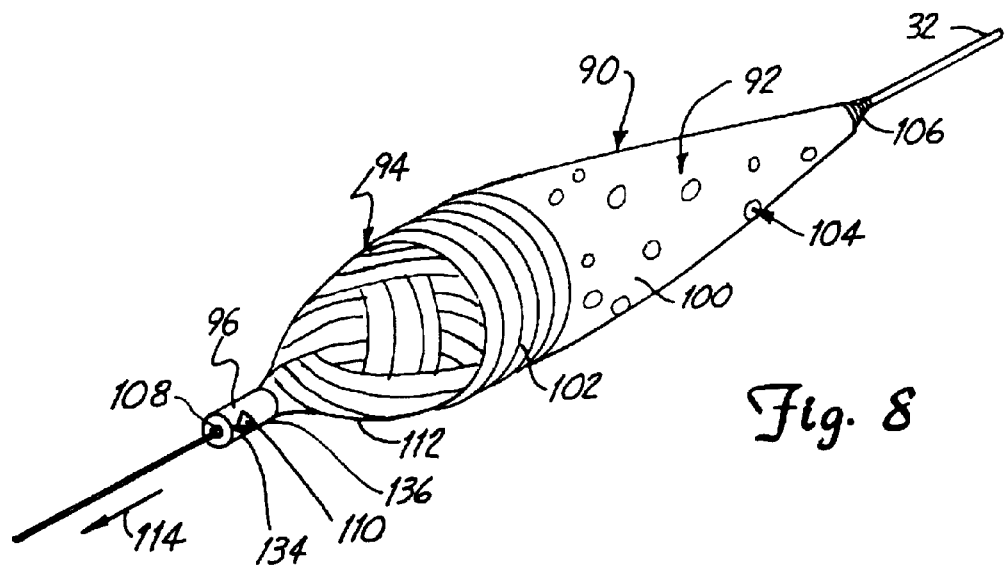
FIG. 8 is a perspective view of an alternate embodiment of a protection device shown in a radially-expanded deployed profile.

FIGS. 8–11 illustrate an alternate embodiment of a protection device 90. As illustrated in FIG. 8, protection device 90 includes a filter 92, a frame 94 and a collar 96. Protection device 90 is operably coupled to a guidewire 32 for operation as will be explained. Guidewire 32 is a typical guidewire having a small diameter for insertion into a tract to a treatment site, and preferably includes a spring coil tip.

Filter 92 includes a cone-shaped porous portion 100 and a pleated portion 102. Porous portion 100 includes a plurality of openings 104 to permit blood flow through filter 92 while restricting flow of debris or particles. A distal tip 106 of filter 92 is fixedly secured to guidewire 32. Preferably, filter portion 100 is formed of a polymer material, such as a polyurethane material, and holes or openings 104 are formed via known laser techniques.

Collar 96 is preferably formed of a relatively short tubular member having an inner lumen 108 and having notches 110 formed on an outer perimeter. Guidewire 32 extends through lumen 108 so collar 96 is slidably coupled to guidewire 32. Frame 94 is coupled to collar 96, and filter 92 is coupled to frame 94.

Preferably, frame 94 is formed of an elongated wire 112 having opposed ends. Opposed ends of wire 112 are coupled to collar 96 to form a mouth, and filter 92 (in particular, pleated portion 102) is coupled to wire 112 along substantially the entire length of wire 112. Preferably, guidewire 32 extends through collar 96 and through the mouth and extends along the entire longitudinal length of filter 92. Thus, collar 96 is moved proximally as illustrated by arrow 114 to collapse the mouth formed by frame 94 for insertion. Collar 96 is slid distally to expand the mouth formed by frame 94 and filter 92 to a deployment position.

Preferably, wire 112 is formed of a relatively elastic material such as Nitinol. Filter portion 102 is secured to wire loop 112 by one of various suitable attachment methods, including adhesives, stitching, or other known methods, to define the mouth of the device 90. Ends of wire 112 are also preferably coupled to collar 96 by known attachment methods, including adhesives.

Preferably, pleated filter portion 102 is formed of a polymer material such as polyurethane. The pleated filter portion 102 is preferably manufactured by winding a wire or other suitable coil around a polymer tube material. After the wire is wound around the tube, the tube is pressurized, causing the tube material to expand between the gaps in the wire, creating the pleats or creases which allow portion 102 to collapse. The coil is then removed, leaving collapsible portion 102. Construction of collapsible portion 102 is described in St. Germain, U.S. Pat. No. 5,534,005, issued Jul. 9, 1997, and assigned to Scimed Life Systems, Inc., hereby incorporated by reference.

The pleated filter portion 102 allows for the filter to expand or extend longitudinally to absorb impact pressure caused by embolic material received by filter portion 92 to maintain the placement of the device 90 during operation. Filter portion 100 and pleated portion 102 may be formed separately or from a single sheet of polymer material.

Figure 9:
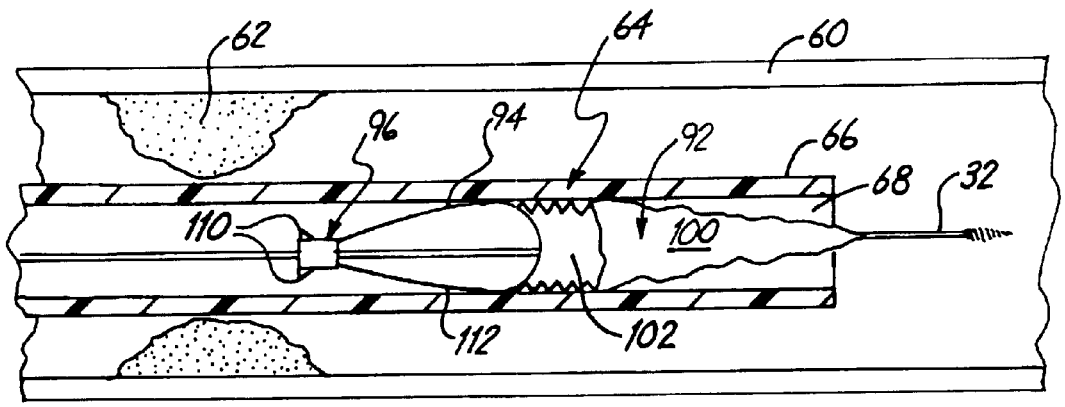
FIG. 9 is a view of the protection device of FIG. 8 in a collapsed profile, inserted into a vessel via an insertion sheath.
Figure 10:
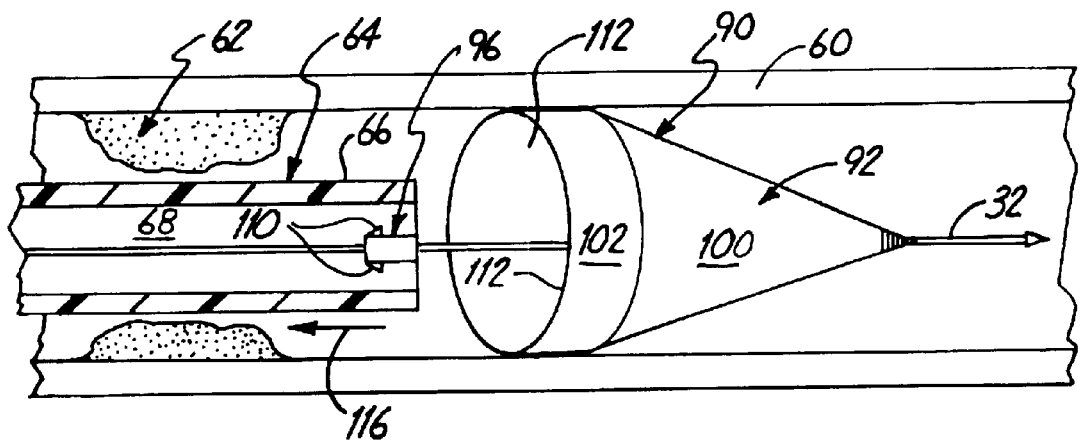
FIG. 10 is a view of the protection device of FIG. 8 in an expanded deployed profile in a vessel, shown with the insertion sheath withdrawn.

FIGS. 9–12 illustrate operation of device 90 in a patient's vasculature. Some parts are similar to those shown in FIGS. 5–7, and similar numbers are used to identify similar parts. As shown in FIG. 9, device 90 is inserted in a collapsed profile in cooperation with an insertion sheath 64 similar to that shown and described in FIG. 5. Tube 66 exerts a force on wire 112 and filter portions 100, 102 to collapse device 90. As illustrated, in the collapsed profile, collar 96 moves along wire 32 to longitudinally accommodate for radial slack of the collapsed device 90. Sheath 64 and device 90 are advanced to a deployment site, preferably distal of a stenotic region 62, for operation during a treatment procedure.

Once device 90 and sheath 64 are located at the deployment site, sheath 64 is withdrawn (while the position of guidewire 32 is maintained) as illustrated by arrow 116 so that the wire 112 expands radially outwardly (since the compression force is released). This causes filter 92 to expand to conform to the inner diameter of the vessel 60. As wire 112 expands outwardly, collar 96 slides distally along guidewire 32 for radial expansion of wire 112 and filter 92. Preferably, as previously explained, wire 112 is formed of a sufficiently elastic material to essentially spring outwardly after pressure is released, so that a tight interference between frame wire 112 and the vessel walls of vessel 60 is maintained. This helps to ensure that the device 90 is sufficiently lodged against vessel wall 60 so that it stays in position during treatment and is not dislodged as a result of blood flow through the filter 92. In particular, sufficient pressure must be maintained so that the filter conforms to the diameter of vessel 60 and does not migrate due to force imparted to the filter when debris collects in the filter and so that no embolic material can slip between the filter and the walls of vessel 60.

Figure 11:
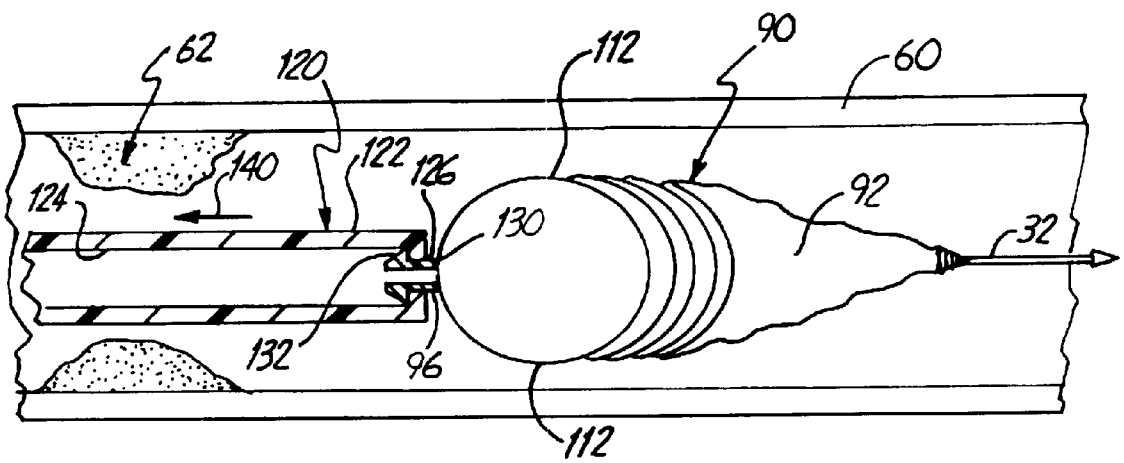
FIG. 11 is a view of the protection device of FIG. 8 in a somewhat collapsed profile being withdrawn from the vessel via a retrieval sheath.
Figure 12:
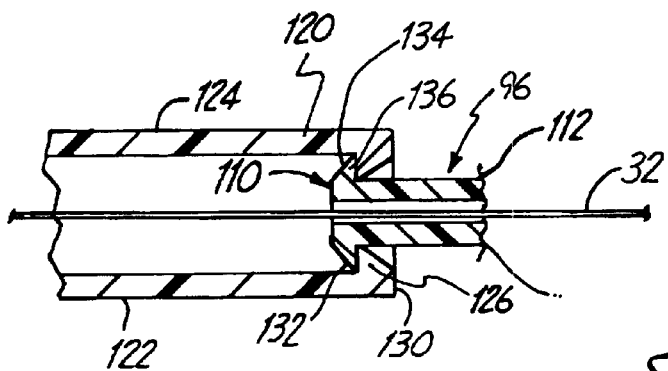
FIG. 12 is a detailed view of portion 120 of the device shown in FIG. 11.

Thereafter, treatment devices (not shown) may be advanced along guidewire 32 for placement relative to a stenosis 62 for treatment. Such treatment devices may include a dilatation catheter, stent delivery catheter or atherectomy or thrombectomy devices, etc. After treatment is completed, device 90 may be withdrawn as illustrated in FIGS. 11 and 12. Device 90 is withdrawn via a retrieval device 120. Retrieval device 120 is formed of a tubular member 122 having an inner lumen 124 and a locking tab 126 formed on an inner surface of the tubular member 122. Locking tab 126 mates with notch 110 formed on collar 96 for retrieval and removal of device 90.

Preferably, locking tab 126 is formed of a rigid extension having a sloped camming surface 130 and a flat locking surface 132. Notch 110 also includes a camming surface 134 and a flat locking surface 136. The camming surfaces 130, 134 are aligned so that, as sheath 120 is advanced, camming surfaces 130, 134 mate to slightly expand tube 122 so that locking member 126 on sheath 120 advances past notch 110 until the locking surfaces 132, 136 align and the camming force is released. This allows tube 122 to collapse to its original dimension with surfaces 132, 136 aligned to lock device 90 to sheath 120 for withdrawing device 90. Sheath 120 is withdrawn proximally, as illustrated by arrow 140, while maintaining the position of guidewire 32. This causes collar 96 to slide proximally to collapse device 90 along guidewire 32 thereby drawing wire 112 down over wire 32 and collapsing device 90. Once device 90 is collapsed, guidewire 32 and sheath 120 are collectively withdrawn to remove collapsed device 90.

FIGS. 13–16 illustrate an alternate embodiment of a protection device 150 where similar numbers are used to identify similar parts of previous embodiments. Device 150 is shown in operation in a vessel 60 having a stenosis 62. Device 150 includes a filter 152, a frame 154, and a collar 156. Device 150 is operably coupled to guidewire 32 for operation. Filter 152 is preferably a cone-shaped member having proximal and distal ends 158, 160. The distal end 160 is generally "V"-shaped. Filter 152 may be formed from a polymer sheet material similar to that described for previous embodiments and filter holes or openings 180 may be formed therein by laser techniques. Material and debris generally collect at the "V"-shaped tip to limit interference with blood flow through filter 152. The "V"-shaped end 160 is fixedly coupled relative to guidewire 32. Proximal end 158 includes an opening which is supported relative to frame 154 to form a mouth of the device, as will be explained. Collar 156 is a tubular member 164 having an inner lumen 166 slidably coupled relative to guidewire 32.

Frame 154 includes a generally circular mouth member 170 and a plurality of struts or ribs 172. Mouth 170 supports filter 152 and is preferably formed of a wire loop which is coupled thereto via a known adhesive or other suitable means. The mouth is coupled to collar 156 via struts or ribs 172 so that the collar slides along guidewire 32 to selectively longitudinally extend device 150 to collapse device 150 for insertion and retrieval, and longitudinally shorten device 150 to expand device 150 (and mouth 170) for deployment. Preferably, struts 172 are attached to collar 156 and mouth 170 by any suitable means. Preferably, frame 154 (mouth 170 and struts or ribs 172) are formed of a wire or strip of a relatively elastic material such as a Nitinol material.

Device 150 includes compression spring 176 to bias device 150 in the longitudinally shortened (and thus radially expanded) profile having mouth 170 radially expanded for operation. In particular, spring 176 includes opposed ends, a first end is attached to collar 156, and a second end is attached to end 160 of filter 152. The compression spring 176 is normally biased to compress as illustrated by arrows 178 to bias the device in an opened deployed profile.

For insertion, device 150 is maintained in a low-profile position via sheath 64 as illustrated in FIG. 13 similar to that described for previous embodiments. In particular, sheath 64 exerts a force on frame 154 and filter 152 to compress frame 154 and filter 152 against the spring bias provided by compression spring 176. As shown in FIG. 13, insertion sheath 64 and device 150 are inserted into a patient and located distal of a stenosis 62 for deployment.

To deploy the device, the sheath 64 is withdrawn while the operator maintains the position of guidewire 32. Once sheath 64 is withdrawn from device 150, frame 154 and filter 152 expands radially outwardly under the force of the compression spring 176 to expand mouth 170 to conform to the vessel walls 60 as illustrated in FIG. 14. Ribs 172 are extended outwardly to support mouth 170 in a radially-expanded position. The spring 176 maintains device 150 in a deployed position so that mouth 170 conforms to the opening of the vessel. Debris is captured and device 150 does not migrate under the load of the debris collected in filter 152.

Figure 15:
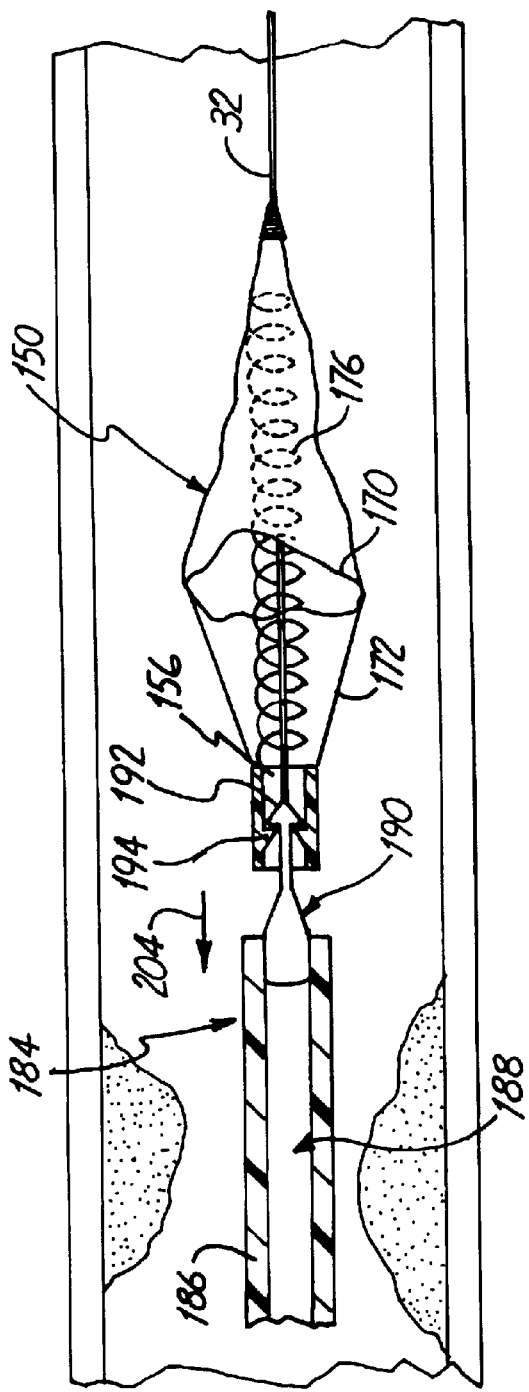
FIG. 15 is a view of the protection device of FIG. 13 in a collapsed profile being withdrawn from the vessel via a retrieval sheath.
Figure 16:
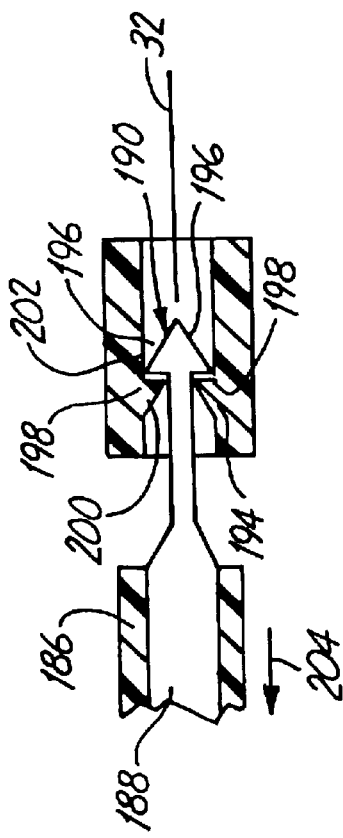
FIG. 16 is a detailed view of portion 16 of the device shown in FIG. 15.
Figure 19:
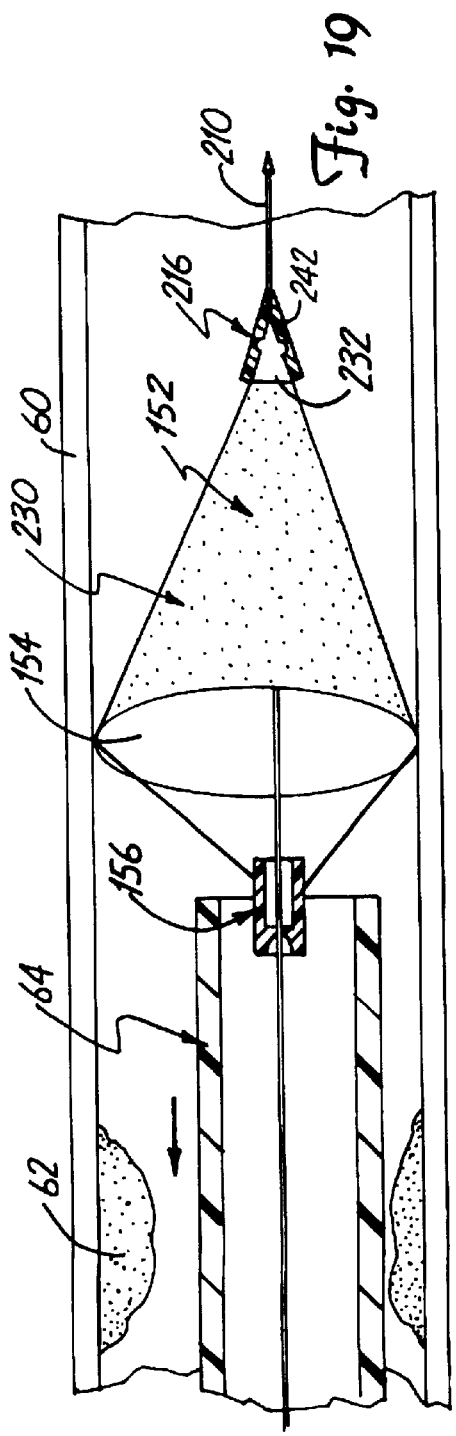
FIG. 19 is a view of the protection device of FIG. 18 in an expanded deployed profile in a vessel, shown with the insertion sheath withdrawn proximally.

After treatment is completed, device 150 may be withdrawn. Preferably, device 150 is withdrawn via a removal sheath 184, as illustrated in FIGS. 15–16. The removal sheath 184 includes an outer tubular extent 186 supporting an inner tube 188. The inner tube 188 includes a docking tip 190. Docking tip 190 includes docking latch 192 which cooperate with a latch 194 formed on an inner surface of collar 156. Docking latch 192 is formed of an arrow tip 190 defining sloped camming surface 196 and a lateral locking surface 198. Latch 194 on collar 156 includes a camming surface 200 and a lateral locking surface 202.

Sheath 184 is advanced over the guidewire 32 to insert tip 190 through the opening in tubular collar 156. Tip 190 is advanced until camming surfaces 196, 200 expand collar 156 to further advance arrow-shaped tip 190 until collar 156 collapses to align locking surfaces 198, 202 to lock device 150 to sheath 184 for withdrawal. After device 150 is locked to sheath 184, retrieval device 184 is first withdrawn proximally, as illustrated by arrow 204, while maintaining the position of guidewire 32 to force the frame 154 and filter 152 against the spring bias to a low-profile dimension. Thereafter, retrieval sheath 184 and guidewire 32 are collectively proximally withdrawn as illustrated to remove the device.

An alternate embodiment of a protective device is illustrated in FIGS. 17–20 and is formed independently of a guidewire 210. Guidewire 210 is formed of an elongated wire 212, preferably having a spring coil tip 214, and a protective device docking member 216 coupled to a distal portion of wire 212, as illustrated in FIG. 17. Docking member 216 is rigidly coupled to wire 212 and in one embodiment is formed of a generally "V"-shaped member 218 including a docking channel 220. Member 218 includes groove 222 which opens to channel 220. Docking member 216 is used to removably secure a protection device thereto as will be explained.

Docking member 216 may be permanently formed on the guidewire 210. Alternatively, docking member 216 may be detachably connected to guidewire 210 such as by a friction fit between guidewire 210 and a channel (not shown) of the docking member 216 or by a mechanical attachment mechanism. If a detachable, docking member 216 may be used on any suitable guidewire, thereby adapting the guidewire for operation with a protection device.

FIG. 18 illustrates an embodiment of a protection device 230 which may be selectively coupled to docking member 216. Protection device 230 includes a distal cone 232, a filter 152, a frame 154, and a collar 156. Cone 232 is coupled to a distal end of filter 152. Cone 232 is generally "V"-shaped and is formed of a rigid member having a distal opening (not shown) sized for insertion of guidewire 210 therethrough. Cone 232 includes a locking ring 242 extending about an outer perimeter of cone 232. Locking ring 242 is sized for insertion into groove 222 of docking member 216.

Thus, device 230 is mounted relative to the guidewire by inserting guidewire 210 through an opening in cone 232. Device 230 is advanced over guidewire 210 to align cone 232 with docking member 216. Cone 232 is forced into channel 220 of docking member 216 until ring 242 snaps into groove 222 and is maintained therein. Device 230 is inserted in a low-profile collapsed condition via cooperation with sheath 64, and is deployed by withdrawing sheath 64 while maintaining the position of guidewire 210 after device 230 is positioned at a treatment site (as comparatively illustrated in FIGS. 18–19) similar to that previously described with reference to FIGS. 13–14.

Figure 20:
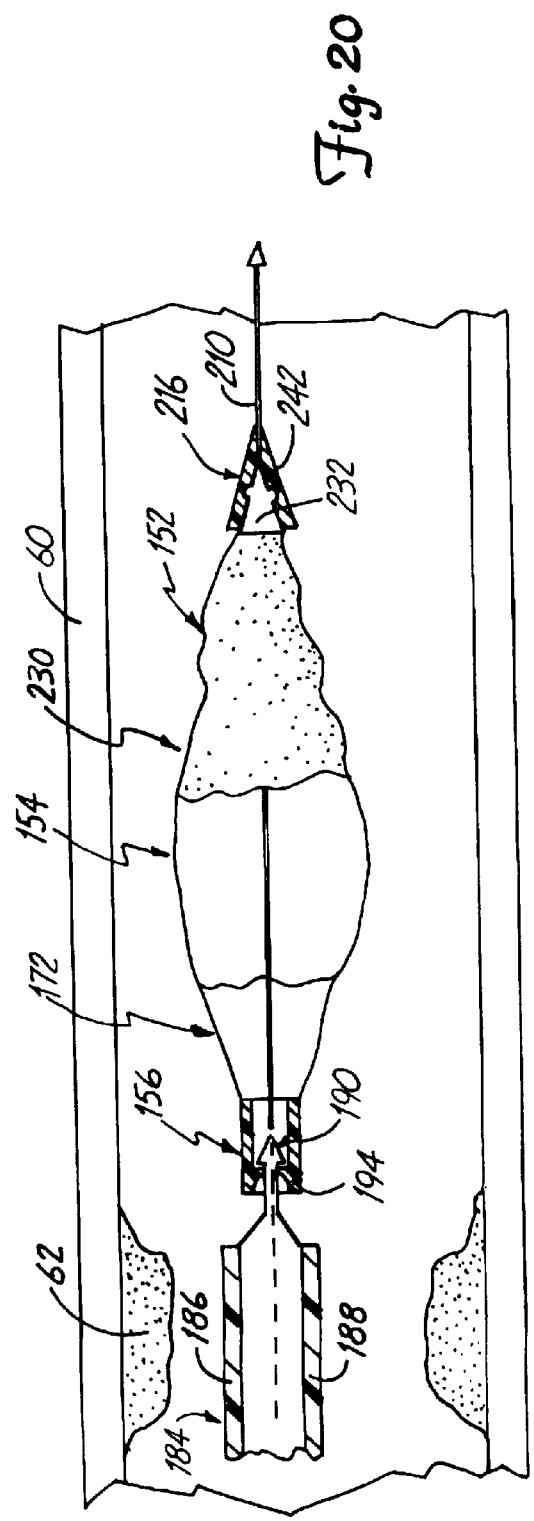
FIG. 20 is a view of the protection device of FIG. 18 in a collapsed profile being withdrawn from the vessel via a retrieval sheath.

FIG. 20 illustrates withdrawal of device 230 via retrieval sheath 184, as previously described with reference to FIGS. 15–16. Sheath 184 is coupled to collar 156 and is then withdrawn proximally while maintaining the position of guidewire 210 to collapse device 230 to a low profile. Thereafter, sheath 184 and guidewire 210 are withdrawn to remove guidewire 210, protection device 230, and sheath 184 from the patient after treatment.

Figure 21:
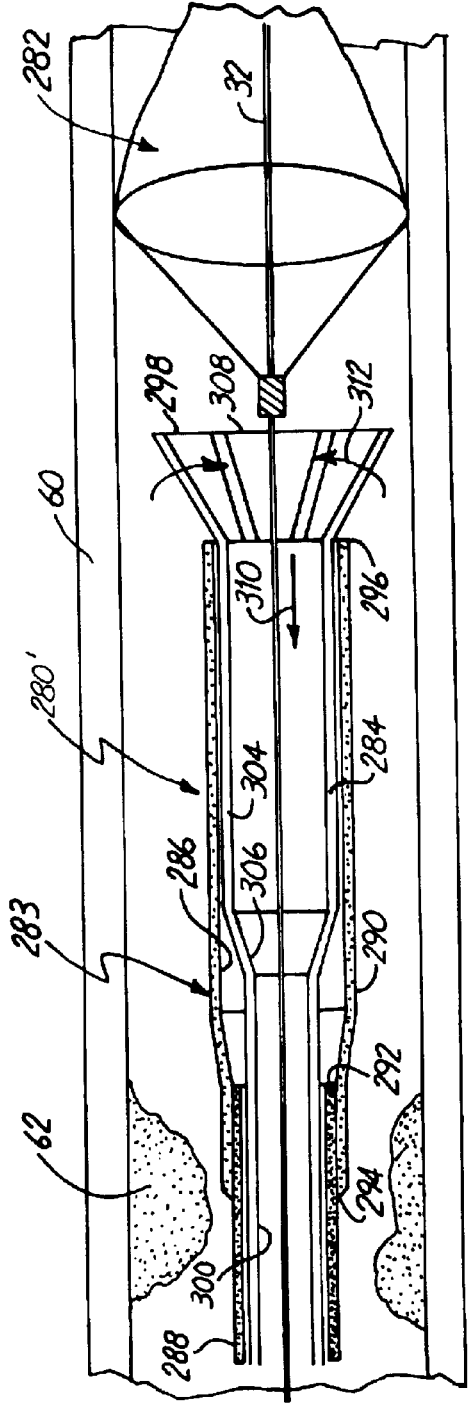
FIG. 21 illustrates an embodiment of a retrieval sheath for withdrawal of a protection device.

FIG. 21 illustrates an embodiment of a retrieval sheath 280 for operation with a distal protection device 282 for collapsing the distal protection device for withdrawal. The retrieval sheath 280 includes a telescoping tubular structure including an outer tubular member 283 and an inner tubular member 284. Outer tubular member 283 includes a lumen 286, and inner tubular member 284 extends through lumen 286 and is movable therein to form the telescoping tubular structure.

Outer tubular member 283 is formed of a composite structure including a first tubular portion 288 and a second tubular portion 290. The first tubular portion 288 includes a proximal end (not shown) and a distal end 292. The second tubular portion 290 includes a proximal end 294 and a distal end 296. Proximal end 294 is coupled to distal end 292 of tubular member 288 to form a composite outer tubular structure 283 having a proximal end (not shown) and distal end 296.

Inner tube 284 includes a proximal end (not shown) and a distal end 298. Inner tube 284 includes a first diameter portion 300, a second diameter portion 304, a transition portion 306, and tapered flanged end 308. First and second portions 300, 304 are coupled via transition portion 306. Flanged end 308 has a relatively large tapered mouth for capturing and progressively collapsing a deployed protection device as will be explained.

The proximal end of inner tube 284 extends through outer tube 283 and exits from proximal end of outer tube 283 for providing a mechanism for slidably moving inner tube 284 within outer tube 283. Flanged end 308 is relatively flexible and resilient and is biased in a radially expanded position so that it opens to an expanded tapered profile, as illustrated in FIG. 21, when flanged end 308 extends beyond distal end 296 of outer tube 283. When flanged end 308 is retracted within inner tube 283 as illustrated via arrow 310, flanged end 308 collapses as illustrated by arrows 312 to assume the dimension of outer tube 283 in a collapsed position (not shown). Flanged end 308 may be formed of a pleated material or simply a relatively elastic material.

In operation, retrieval sheath 280 is inserted into a patient's vasculature with flanged end 308 in a collapsed position within inner tube 283 to provide a low profile for insertion. Retrieval sheath 280 is inserted and aligned closely proximate to deployed protection device 282. Once retrieval device 280 is aligned, inner tube 284 is slid distally relative to outer tube 282 to expand flanged end 308 to an expanded profile, as illustrated in FIG. 21, to surround the deployed protection device. Thereafter, sheath 280 may be advanced, or protection device 282 may be withdrawn proximally via guidewire 32 to forcibly collapse protection device 282 as protection device 282 is withdrawn along the tapered inner channel of flanged end 308. Retrieval device 280, protection device 282, and guidewire 32 are then withdrawn. The device thus provides a system for capturing a protection device 282 and filtered contents (debris, emboli, etc.) along therewith to minimize post-procedural embolic events. Preferably, inner and outer tubes 282, 284 are formed of a polymer material, and flanged end 308 is formed of a polymer membrane. Although a particular embodiment of retrieval device 280 is shown, it should be understood that construction of device 280 is not limited to the exact construction shown.

Figure 22:
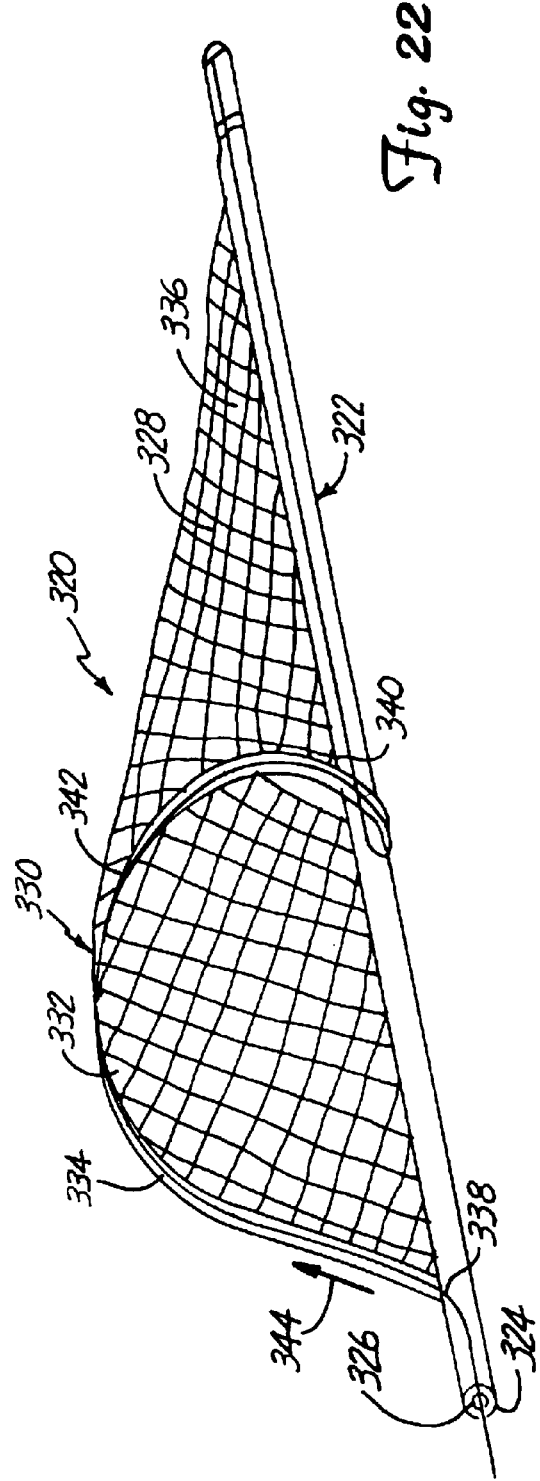
FIG. 22 is a perspective view of an alternate embodiment of a protection device, coupled to a guidewire in an expanded deployed profile.

FIGS. 22–24 illustrate an alternate embodiment of a distal protection device 320. As shown in FIG. 23, distal protection device 320 is coupled to a guidewire 322 to operate between a radially-expanded deployed profile illustrated in FIGS. 22 and 24, and a collapsed profile illustrated in FIG. 23 for insertion and retrieval. Guidewire 322 is formed of a tubular member 324 including a central lumen 326 therethrough. The guidewire 322 may be formed of a hypo tube or other material. The distal protection device 320 includes a filter 328 and a frame 330.

Preferably, frame 330 is formed of an elongate wire 332 and a polymer sleeve 334. Frame 330 is coupled to guidewire 322 and is supported thereby between the insertion dimension illustrated in FIG. 23 and the deployed dimension illustrated in FIGS. 22 and 24. Filter 328 is coupled to frame 330 and is supported thereby at its proximal end by frame 330. Filter 328 may be formed of a polymer sheet material or a mesh-like material having holes or openings 336 therein to allow blood to flow therethrough while restricting flow of emboli, debris and clotting material. Filter 328 is cone-shaped, preferably having a "V"-shaped tip and a large opening to funnel debris for collection. Filter 328 and sleeve 334 may be integrally or separately formed, and secured via known attachment methods such as known adhesives.

Guidewire 322 includes spaced distal openings 338, 340 which communicates with inner lumen 326. Opposed ends of sleeve 334 are coupled to spaced openings 338, 340 so the lumen through sleeve 334 forms a path for frame wire 332. Frame wire 332 extends from a proximal end (not shown) of the guidewire 322 through lumen 326, through openings 338 and 340, and is anchored at a distal end of lumen 326 (preferably proximate to opening 340). Frame wire 332 also extends through sleeve 334 to form an external loop 342 defining the mouth of the protection device 320. External loop 342 is tightened by pulling the wire 332 proximally, and is opened by pushing the wire 332 distally, as illustrated by arrow 344, to open and close the mouth of protection device 320.

FIGS. 23–24 illustrate operation of protection device 320. As illustrated in FIG. 23, the device is inserted in a low-profile dimension by proximally retracting wire 332 to close external loop 342 to locate device 320 at a deployment site, preferably distal of a stenosis 62. Frame wire 332 is moved distally as illustrated by arrow 344 to expand loop 342 to open the mouth to filter 328 to conform to the dimension of vascular lumen 60, as illustrated in FIG. 24. As the mouth of the device 320 is expanded to conform to the vascular dimension, guidewire 322 pushes against a lumen wall to provide a tight fit between filter 328 and vascular wall 60.

The mouth has a dimension which conforms to the vascular wall, and cone-shaped filter 328 funnels material to a tip of the filter to allow bloodflow to continue therethrough. Device 320 is collapsed after use for removal. To collapse the device for withdrawal, frame wire 332 is moved proximally, as illustrated by arrow 346 in FIG. 24, to collapse or close external loop 342 to the low-profile collapsed dimension illustrated in FIG. 23.

In the embodiment illustrated in FIGS. 23–24, a pressure-sensing device 350 may be inserted through lumen 326 of guidewire 322. The pressure-sensing device 350 is formed of an elongated member 352 having a distal tip 354 which is curve-shaped to align a pressure sensor facing the direction of blood flow or fluid flow through vessel 60. Proximal circuitry is coupled to the pressure sensor at distal tip 354 to provide a pressure reading to an operator. Of course, device 350 may simply be a hollow tube with the pressure sensing mechanism located entirely at a proximal end of device 350. The pressure reading indicates whether the blood vessel or vascular vessel 60 is occluded distal of protection device 320, to ensure proper blood flow through protection device 320. Thus, if emboli, particles, or debris clogs filter 328 of distal protection device 320, the pressure will drop, thus indicating restricted blood flow for real-time monitoring of blood flow through the distal protection device 320. Use of a pressure sensor provides advantages over use of dye-injection techniques to provide continuous real-time quantitative measurement of blood flow for monitoring operation.

Although the protection devices described are illustrated for use as temporary filters, it should be understood that the devices of the present invention are not so limited and may be used for permanent filters which are retained in a patient to filter debris and clotting material. Although the present invention has been described with reference to preferred embodiments, workers skilled in the art will recognize that changes may be made in form and detail without departing from the spirit and scope of the invention.

What is claimed is:

1. Apparatus for filtering emboli from blood flowing through a vessel, the apparatus comprising:

a guide wire having a distal region and a docking member rigidly coupled to the distal region;

a distal cone disposed for translation on the guide wire, the docking member limiting translation of the distal cone in a distal direction; and a filter sac connected to the distal cone, wherein the distal cone can be removably coupled to the docking member.

2. The apparatus of claim 1 wherein, when the filter sac is deployed in the vessel, rotation or distal translation of the guide wire relative to the distal cone does not displace the filter sac, but retraction of the guide wire in a proximal direction causes the docking member to abut against the distal cone.

3. The apparatus of claim 1 wherein the docking member contains a grove and the distal cone contains a locking ring sized for insertion into the grove.

4. Apparatus for filtering emboli from blood flowing through a vessel, the apparatus comprising:

a guide wire having a first portion having a first diameter and a distal region having a second diameter greater than the first diameter; and a filter element having a distal cone disposed for translation on the first portion, the distal cone having an aperture greater than the first diameter but smaller than the second diameter, wherein rotation or distal translation of the guide wire relative to the distal cone does not displace the filter element, and distal cone can be removably coupled to the docking member.

5. The apparatus of claim 4 wherein the guide wire further comprises a flange disposed on the distal region having a diameter larger than the diameter of the aperture in the distal cone.

6. Apparatus for filtering emboli during treatment of occlusive disease in a vessel, the apparatus comprising:

a guide wire having a first diameter and a distal region having a second diameter greater than the first diameter;

a filter element having a sac coupled to a distal cone, the distal cone having an aperture greater than the first diameter but smaller than the second diameter, wherein the filter element is disposed on the guide wire and the guide wire extends through the aperture with the distal region disposed distally of the distal cone, so that when the filter element is deployed in the vessel, rotation or distal translation of the guide wire does not displace the filter element, but retraction of the guide wire in a proximal direction causes the distal region to abut against the distal cone, and wherein the distal cone can be removably coupled to the docking member.

7. A method of filtering emboli from blood flowing through a vessel, the method comprising:

providing a guide wire having a distal region including a docking member, and a filter element having a distal cone disposed for translation on the guide wire proximal of the docking member, wherein the distal cone can be removably coupled to the docking member;

transluminally inserting the guide wire and filter element into a vessel;

deploying the filter element to engage a wall of the vessel, the filter element filtering emboli out of blood flowing through the vessel;

advancing a treatment device along the guide wire to treat a portion of the vessel proximal to the location of the filter element, rotation or distal translation of the guide wire relative to the filter element imparted by the treatment device not displacing the filter element.

8. The method of 7 wherein:

the docking member contains a grove and the distal cone contains a locking ring sized for insertion into the grove; and the locking ring of the distal cone is inserted into the grove of the docking member until the locking ring is wholly within the grove.

9. The method of claim 7 further comprising:

providing a delivery sheath; and compressing the filter element to a contracted state to insert the filter element within the delivery sheath.

10. The method of claim 9 wherein the filter element comprises an expandable sac, and deploying the filter element comprises expanding the expandable sac so that a perimeter of the expandable sac contacts the wall of the vessel.

11. Apparatus for filtering emboli from blood flowing through a vessel, the apparatus comprising:

a guide wire having a distal region;

a filter element disposed for rotation on the distal region of the guide wire, the filter element comprising a self-expanding strut and a filter sac connected to the self-expanding strut; and a docking member rigidly coupled to the distal region distal to the filter element, the docking member limiting distal translation of the filter element on the guide wire, wherein the filter element can be removably coupled to the docking member.

12. The apparatus of claim 11 wherein, when the filter sac is deployed in the vessel, rotation of the guide wire does not displace the filter element.

13. The apparatus of claim 11 wherein the docking member contains a groove and the filter element contains a locking ring sized for insertion into the groove.

14. A method of filtering emboli from blood flowing through a vessel, the method comprising:

providing a guide wire having a distal region including a docking member rigidly coupled to the distal region, and a filter element disposed for translation on the guide wire proximal to the docking member, the filter element comprising a plurality of self-expanding struts having a filter sac affixed thereto, wherein the filter element can be removably coupled to the docking member;

transluminally inserting the guide wire and filter element into a vessel;

deploying the filter element so that the struts and filter sac expand to engage a wall of the vessel, the filter sac filtering emboli out of blood flowing through the vessel; and advancing a treatment device along the guide wire to treat a portion of the vessel proximal to the location of the filter element, rotation or distal translation of the guide wire relative to the filter element imparted by the treatment device not displacing the filter element.

15. The method of claim 14 further comprising retracting the guide wire in a proximal direction to cause the docking member to abut against the filter element.

16. The method of claim 14 wherein the docking member contains a groove and the filter element contains a locking ring sized for insertion into the groove.

17. The method of claim 14 further comprising:

providing a retrieval catheter having a recovery sock;

advancing the retrieval catheter over the guide wire until the recovery sock covers a mouth of the filter element; and urging the retrieval catheter against the self-expanding struts of the filter element to cause the filter element to collapse.

* * * * *